United States Patent [19]

Natori

[11] Patent Number: 4,960,756
[45] Date of Patent: Oct. 2, 1990

[54] LECTIN LIKE PROTEIN SUBSTANCE, METHOD OF OBTAINING SAME AND ANTI-TUMOR AGENT COMPRISING SAME

[75] Inventor: Shunji Natori, Tone, Japan

[73] Assignee: Sanwa Kagaku Kenkyusho Co., Ltd., Nagoya, Japan

[21] Appl. No.: 90,730

[22] Filed: Aug. 28, 1987

[30] Foreign Application Priority Data

Sep. 13, 1986 [JP] Japan .................. 61-216158

[51] Int. Cl.$^5$ .................. A61K 37/10; C07K 3/00
[52] U.S. Cl. .................. 514/8; 530/396
[58] Field of Search .................. 514/8; 530/396

[56] References Cited

FOREIGN PATENT DOCUMENTS 59-13730  1/1984  Japan .
59-222422 12/1984 Japan .
61-105621 6/1985  Japan .
60-209530 10/1985 Japan .

OTHER PUBLICATIONS

H. Komano et al., J. Biol. Chem. 255: 2919–2924, 1980.
A. Itoh et al., J. Biochem. 99: 9–15, 1986.

Primary Examiner—John W. Rollins
Attorney, Agent, or Firm—Armstrong, Nikaido, Marmelstein, Kubovcik & Murray

[57] ABSTRACT

A lectin like protein substance, method of obtaining same and a pharmaceutical agent containing the substance, as an effective ingredient. The substance is obtained through steps of cultivating a cell line stablished from *Sarcophaga peregrina* embryo to produce the substance in a culture medium, as product of the cell line, separating the refining the same. The substance shows an anti-tumor activity and thus is useful as an effective ingredient for medicines to cure cancers.

1 Claim, 4 Drawing Sheets

A: Added final purified sample treated by Sepharose column

B: Added sample treated by butyl-toyopearl column

C: Added sample treated by DEAE-Cellulose column

D: Added sample treated by CM-Cellulose column

E: Control (non treated)

●: Molecular weight marker
 1: MW = 58000
 2: MW = 52000
 3: MW = 31000
 4: MW = 20000
 5: MW = 12000

LECTIN LIKE PROTEIN SUBSTANCE, METHOD OF OBTAINING SAME AND ANTI-TUMOR AGENT COMPRISING SAME

BACKGROUND OF THE INVENTION

1. Field of the Invention

The present invention relates to a novel lectin like protein substance, method of obtaining same and anti-tumor agent comprising the same as an effective ingredient. The substance is produced through a cultivation of an insect cell and more particularly a cell line established from flesh fly (*Sarcophaga peregrina*) embryo.

2. Related Arts

The term of "Lectin" is a general one meaning glycoproteins found in animals, plants and bacteria inclusive of virus, excepting those of products due to an immunoreaction and some of the lectins obtained from plants had been known for long to behave as a hemagglutinin. Recently, however, various lectins have been found not only in the plants, but also in animals, and physical significance and characteristics thereof have occupied the attention in the pharmacological field, since some of them shows an agglutination specific not only to erythrocyte, but also leucocyte, cancer cell and the like (for instance, Jap. Pat. Appln. No. 212436/1983 corresponding to Jap. Unexamined Pat. Appln. Gazette No. 105621/1960).

The present inventor has also found a substance from one of insecta, *Sarcophaga peregrina*, which substance shows lectin like activities, activates a macropharge in vitro to produce a tumor killing substance and has been named as "Sarcophaga-Lectin" (Jap. Pat. Appln. Nos. 123298/1982, 94972/1983 and 66330/1984 which correspond to Jap. Unexamined Pat. Appln. Gazette Nos. 13730/1984, 222422/1984 and 209530/1985, respectively).

As anti-tumor agents, chemotherapeutic agents, immunotherapeutic agents and the like have been clinically employed now but those have a relatively high side effect and thus it is anxious for to develop other anti-tumor agents which have a higher safety.

While, the Sarcophaga-Lectin as referred to has been expected as one of high safety anti-tumor agents but has difficulties in its productivity inclusive of insurance of the raw material, isolation and purification.

SUMMARY OF THE INVENTION

An object of the invention lies in isolating and purifying a substance having an anti-tumor activity, with use of a cell line established from *Sarcophaga peregrina* embryo.

Another object of the invention is to provide an industrially acceptable method of obtaining such a substance.

A still other object of the invention is to provide an anti-tumor agent comprising the substance to cure a tumor, cancer and the like.

According to the invention, the first object can be attained by an anti-tumor physicoactive substance produced by the cell line established from *Sarcophaga peregrina* embryo, characterized in that (a) a molecular weight measured by gel-filtration method is about 185,000, (b) an analysis by SDS-gel electrophoresis method shows 4 molecules of subunit having molecular weight of about 32,000 and 2 molecules of subunit having molecular weight of about 30,000, and (c) it co-exists with an inhibitor in a culture medium and shows a hemagglutination and the like lectin like activities, when the inhibitor is removed.

According to the method of the invention, the substance can be obtained through steps of subjecting a supernatant liquid of a culture solution for the cell line established from *Sarcophaga peregrina* embryo to an ion-exchange chromatography, subjecting desired fractions to a hydrophobic chromatography to collect the substance through an adsorption, elution and fractioning, removing an inhibitor from the substance, and subjecting desired fractions to an affinity chromatography to purify the substance through an adsorption, elution and fractionation.

The ion-exchange chromatography may be carried out with use of CM-cellulose column and phosphate buffer to recover a pass-through fraction. The separation of inhibitor may be carried out by passing the fractions to a hydrophobic chromatography column filled with an adsorbent of butyl-toyopearl 650M to cause an adsorption of the desired substance and passing out the inhibitor. The affinity chromatography may be carried out with use of a column filled with an adsorbent of galactose or lactose bound Sepharose 6B to adsorb the desired substance.

EFFECTS OR ADVANTAGES OF THE INVENTION

The substance according to the invention shows in vivo (animal test) an inhibition to a proliferation of solid cancer (Meth-A) cells and ascites cancer (Sarcoma 180) cells to prolong a life of or cure the cancered animal.

According to the method of the invention, such a substance is produced starting from a culture medium of cell line established from *Sarcophaga peregrina* embryo and thus it is possible to mass-produce the substance by a large scale cultivation of the cell line.

Further, the substance may also be expected to utilize as a diagnostic reagent on tumors.

DETAILED DESCRIPTION OF PREFERRED EMBODIMENT

Figure 1:
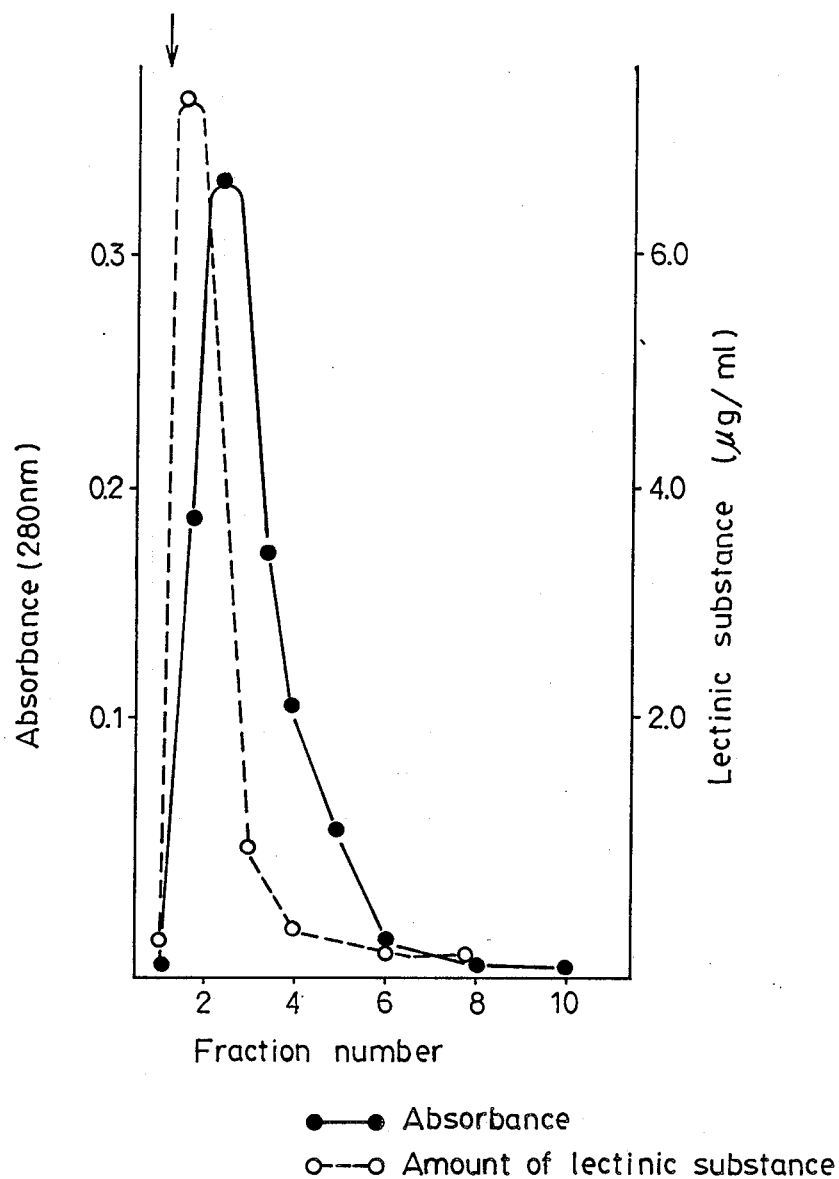
FIG. 1 shows an eluting hydrophobic chromatogram pattern eluted a crude sample by 10% amount of saturated ammonium sulfate containing phosphoric buffered solution.

The invention will now be further explained with reference to an Example for obtaining a lectinic protein substance, Pharmacological Test Examples and a Medicine Manufacturing Example.

EXAMPLE (a) Cultivation of cell line established from *Sarcophaga peregrina* embryo In a culture medium (TC-Yeastlate 5.0 g/l, lactoalbumin hydrolysate 9.5 g/l, table salt 7.0 g/l, potassium chloride 0.2 g/l, glucose 4.0 g/l, sodium monohydrogen phosphate 0.27 g/l, sodium hydrogen carbonate 0.12 g/l, magnesium chloride 0.05 g/l, and calcium chloride 0.2 g/l), cell line established from *Sarcophaga peregrina* embryo were inoculated in an amount of $1 \times 10^6$ per ml of the culture medium, and cultivated at 25° C. for 7 to 10 days. A passage was done, when the number of cells reached $2 \times 10^7$/ml and the culture medium was recovered through a centrifugal treatment.

(b) Separation and purification of a lectin like substance

A dialysis of 1 litre of the culture medium obtained through the operation described in said Item (a) was carried out to 10 mM phosphate buffer (pH 6.0). The resulting solution was chromatographed with use of CM-cellulose column (3.4×17 cm) and washed with the phophate buffer to recover pass-through fraction.

The recovered fractions were combined and saturated ammonium sulfate solution was added thereto, so as to make its final concentration to 20(W/V)%. The resulting solution was adsorbed in a column (1.7×8.3 cm) filled with butyl-toyopearl 650M. Through this operation, an inhibitor combined with a lectin like substance according to the invention was separated therefrom, since it shifts to a pass-through fraction. The column was sufficiently washed with phosphate buffered saline containing 20% amount of saturated ammonium sulfate. Then the adsorptive was eluted with phosphate buffered saline containing 10% amount of saturated ammonium sulfate to recover the elute as each fraction of 5 ml. A chromatogram showing each fraction, absorbance and results of radio immunoassay is given in FIG. 1. In the Figure, an arrow shows the point flowed out the phosphate buffered saline containing 10% amount of saturated ammonium sulfate.

As apparently seen from the Figure, the lectin like substance is eluted just before the main peak of proteins. The recovery on this column was 99%.

A dialysis of the fractions containing the lectin like substance was carried out to a Buffered Insect Saline (Tris buffer containing 130 mM NaCl, 5 mM KCl and 1 mM $CaCl_2$; this saline will be referred to hereinafter as —BIS—). The resulting solution was adsorbed by making lactose bound Sepharose 6B column (1.5×5.0 cm). The column was sufficiently washed with BIS and then the adsorptive was eluted with BIS containing 0.2M galactose to recover the elute as each fraction of 3 ml.

Figure 2:
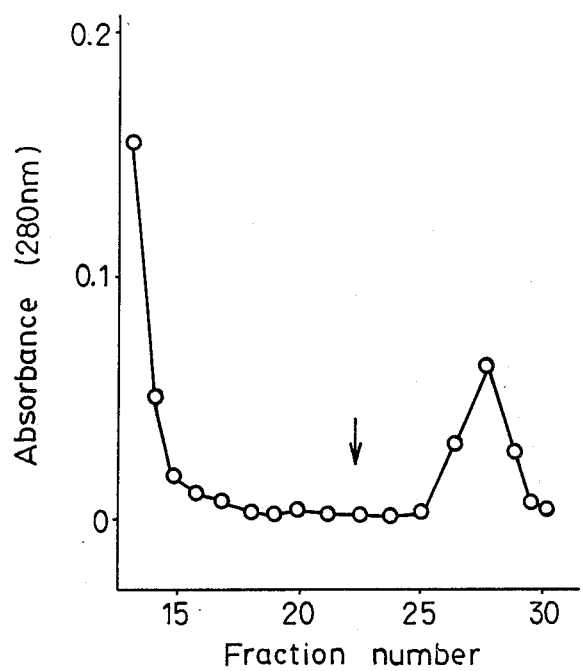
FIG. 2 shows an eluting affinity chromatogram pattern eluted a purified sample by galactose containing buffered insect saline solution.

A chromatogram showing fractions and absorbance thereof is given in FIG. 2. In the Figure, an arrow shows the point flowed out the BIS containing 0.2M galactose. The fractions eluted with the BIS containing 0.2M galactose were combined and dialysed to refine the desired lectin like substance by separating same from galactose.

According to the operations as above, about 1 mg of the purified product was obtained.

Figure 3:
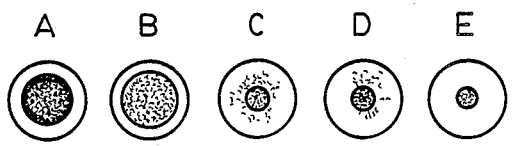
FIG. 3 is illustrations which drawn-up to show an appearance of hemagglutination in each sample, when the sample obtained in each of various purifying stages for obtaining a lectin like protein substance of the invention was added into a blood to check a hemagglutination activity of each sample.

(c) Identification of the product as a hemagglutinin and estimation of its molecular weight As to each sample obtained in each purifying stage in the operations as described in said Item (b), a hemagglutination activity was measured in accordance with a method described by Komano et al ["J. Biol. Chem." Vol. 255, pages 2919–2924]. Results are shown in FIG. 3. It can be seen from the Figure that the products later than the product treated by butyl-toyopearl column show the hemagglutination activity.

Figure 4:
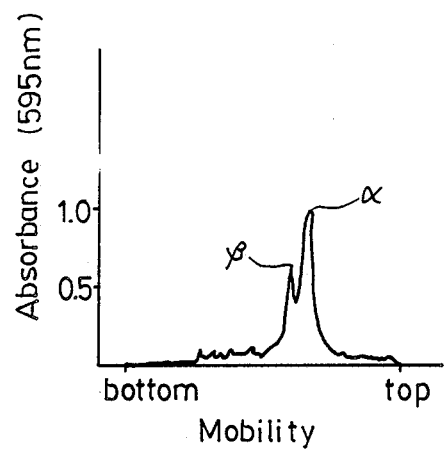
FIG. 4 is SDS-gel electrophoresis pattern of the purified sample.
Figure 5:
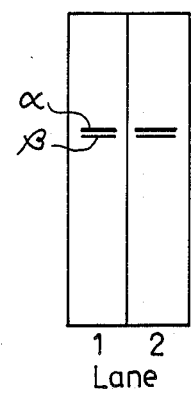
FIG. 5 is a graph showing a result of densitometric scan of two bands in the pattern of FIG. 4.
Figure 6:
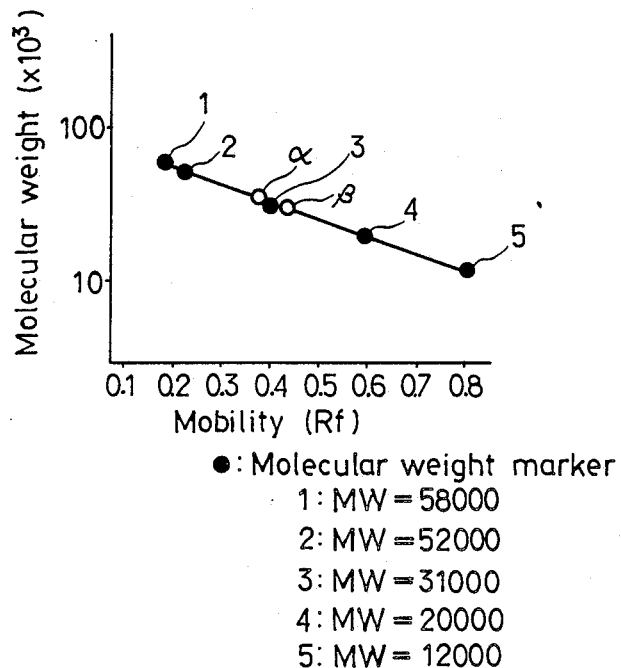
FIG. 6 is a graph showing results of molecular weight determination made on subunits according to SDS-gel electrophoresis method, together with various molecular weight markers.

The final purified sample was analyzed with SDS-polyacrylamide gel electrophoresis to obtain a pattern shown in FIG. 4. In the Figure, lanes 1 and 2 are different preparations, but shows a same pattern with two bands, respectively. Therefore, the gel of lane 1 was scanned with use of a densitometer to obtain a graph shown in FIG. 5. It can be found from this Figure that a ratio of the two bands monitored with a densitometer was 2:1. To determine a molecular weight of each of subunits ($\alpha$ and $\beta$) corresponding to said bands was subjected to electrophoresis with E. Coli ATPase consisting of 5 subunits of known molecular weights, as molecular weight markers, namely 1 (MW=58,000), 2 (MW=52,000), 3 (MW=31,000), 4 (MW=20,000) and 5 (MW=12,000). Results are shown in FIG. 6. As seen from the Figure, the molecular weights of the subunits $\alpha$ and $\beta$ are about 32,000 and 30,000, respectively.

While, another determination of molecular weight on the final purified sample by gel-filtration method with use of Biogel P-300 showed the value of about 185,000. By taking this fact into consideration, it is so estimated that the lectin like substance according to the invention constitutes hexamer by association of 4 pieces of the subunit having molecular weight of 32,000 and 2 pieces of the subunit having molecular weight of 30,000.

PHARMACOLOGICAL TEST EXAMPLE 1

The lectin like substance obtained through the operations described in the Example (final refined product) was dissolved into saline. The resulting solution was injected subcutaneously or intra peritoneally to BALB/c mice and ICR mice over 10 days in dosing amount of more than 100 µg/kg/day. Then, the animals were killed and subjected to an autopsy but no specific necrosis, inflammation or the like was recognized. Further, no anaphylactic shock was obserbed.

PHARMACOLOGICAL TEST EXAMPLE 2 (ANTI-TUMOR ACTION)

Experiment A (To Meth-A cells)

To male BALB/c mice (6 heads for testing and control groups), $2 \times 10^5$ cells of Meth-A cell as a syngenic tumor were transplanted subcutaneously at right side of chest to form a solid cancer. In a period of from 6th day to 20th day from transplantation, 50 µg of the lectin like substance according to the invention and dissolved in saline were injected in or around the cancer portion, on alternate days. A diameter of the forcedly formed solid cancer was measured with use of a slide caliper and recorded.

To the control group, saline was injected, which contains no lectin like substance.

Figure 7:
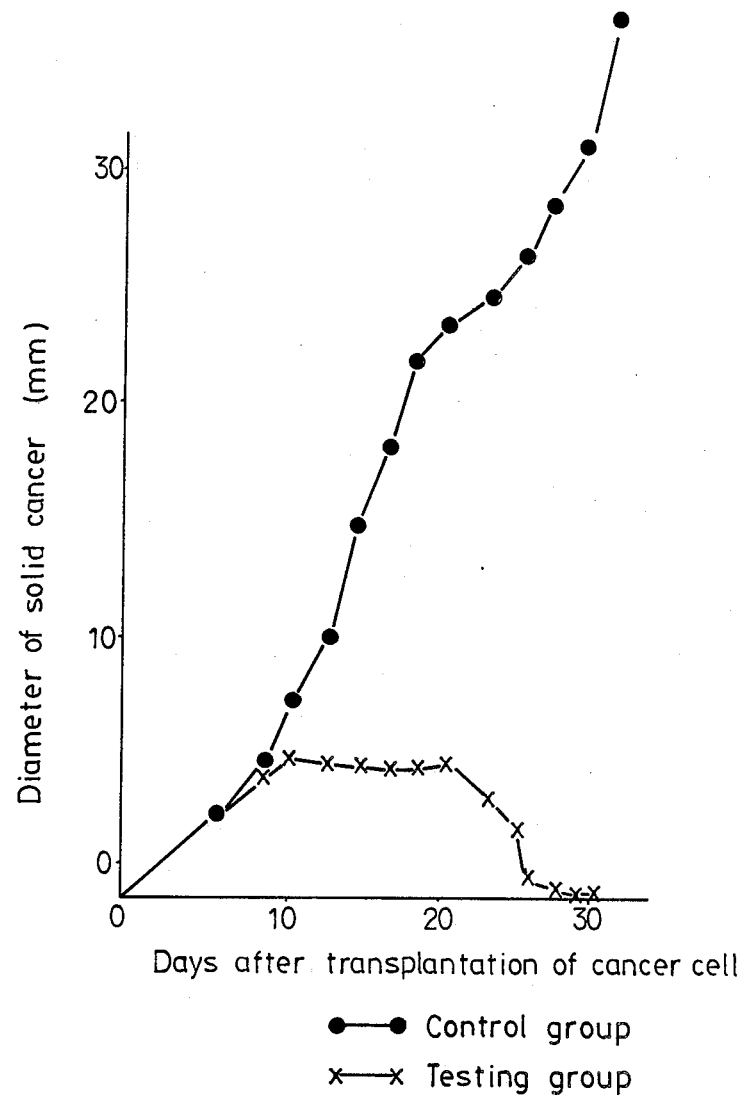
FIG. 7 is a graph showing a progress of inhibition to a solid cancer, when the purified sample is administered to mice.

Results are shown in FIG. 7. As seen from the Figure, it was observed that in the testing group, the solid cancer was completely disappeared, after 30th day from the cancer cell transplantation.

Experiment B (To Sarcoma 180 cells)

To ICR mice, $1 \times 10^5$ cells of Sarcoma 180 cell as an ascites cancer cell were transplanted into an abdominal pore to form an acites cancer. The lectin like substance according to the invention was dissolved into saline to prepare 250 μg/ml solution and 400 μl thereof were administered to each testing animal, after 1 day or 2 days from the transplantation. Head number of living mice, after 30 days from the transplantation is shown in following Table.

| Group | Heads of living animal |
| --- | --- |
| Control | 0/8 |
| Test 1 (dosed in 2nd day) | 6/7 |
| Test 2 (dosed in 3rd day) | 5/6 |

From the results given in the above Table, it was evaluated that the lectin like substance according to the invention is effective also against the ascites cancer.

MEDICINE MANUFACTURING EXAMPLE (DRY POWDER FOR INJECTION)

The lectin like substance according to the invention was dissolved in aqua pro injection to prepare 1 to 10 mg/ml solution. To the resulting solution, mannitol was added, to make a concentration of the mannitol to about 2%. The solution was treated with use of a bacteria removing filter, charged into each vial by 2 ml and freeze dried the solution.

When using for injection, the dried powder is dissolved into saline, aqua pro injection or the like.

What is claimed is:

1. A method for obtaining an anti-tumor, physicoactive substance having haemagglutination and lectin like activities from a cell culture medium wherein said substance co-exists with an inhibitor thereof, said substance:
   (a) having a molecular weight of about 185,000 as determined by gel filtration; and
   (b) having four subunits with a molecular weight of about 32,000 and two subunits with a molecular weight of about 30,000 as determined by SDS-PAGE; said method comprising:
   (1) dialyzing a supernatant liquid of a culture medium of a cell line established from *Sarcophaga peregrina* against 10 mM phosphate buffer, pH6;
   (2) chromatographing said dialyzed liquid on a CMC ion-exchange column, eluting with phosphate buffer, solution, pH 6.0;
   (3) combining the eluates from step (2), and adding saturated ammonium sulfate to prepare a 20 (w/v)% solution;
   (4) introducing said solution onto a chromatography column packed with butyl-toyopearl 650M and washing with phosphate buffered 20% ammonium sulfate solution to remove said inhibitor;
   (5) eluting the column with 10% ammonium sulfate solution and collecting the fractions;
   (6) dialyzing the collected fractions against buffered insect saline;
   (7) purifying the dialyzed fractions by affinity chromatography on a column packed with Sepharose 6B having a ligand selected from the group consisting of galactose, lactose and mixtures thereof; and
   (8) eluting the collected adsorptive with buffered insect saline and fractionating the elute containing the substance.

* * * * *